(12) United States Patent
Saaski et al.

(10) Patent No.: US 10,444,137 B2
(45) Date of Patent: Oct. 15, 2019

(54) BIOAEROSOL DETECTOR HAVING SAFEGUARDS

(71) Applicant: CBRN INTERNATIONAL, LTD., Dubai (AE)

(72) Inventors: Elric Saaski, Monroe, WA (US); Dor Yacobi, Kenmore, WA (US)

(73) Assignee: CBRN INTERNATIONAL, LTD., Dubai (AE)

( * ) Notice: Subject to any disclaimer, the term of this patent is extended or adjusted under 35 U.S.C. 154(b) by 0 days.

(21) Appl. No.: 15/946,588

(22) Filed: Apr. 5, 2018

(65) Prior Publication Data
US 2019/0226973 A1     Jul. 25, 2019

Related U.S. Application Data

(60) Provisional application No. 62/620,980, filed on Jan. 23, 2018.

(51) Int. Cl.
*G01N 21/17*     (2006.01)
*G01N 15/14*     (2006.01)
(Continued)

(52) U.S. Cl.
CPC ..... *G01N 15/1434* (2013.01); *G01N 15/0205* (2013.01); *G01N 15/06* (2013.01); *G01N 2015/0693* (2013.01)

(58) Field of Classification Search
CPC .............. G01N 21/64; G01N 21/6402; G01N 21/6404; G01N 21/6408; G01N 21/6428; G01N 2021/6419; G01N 21/6486
See application file for complete search history.

(56) References Cited

U.S. PATENT DOCUMENTS 4,542,295 A * 9/1985 Mattson ................... G01J 1/42
                                                         250/338.1
4,798,465 A * 1/1989 Knollenberg ...... G01N 15/0205
                                                         356/336
(Continued)

FOREIGN PATENT DOCUMENTS

CN    1401788     3/2003
GB    2544196    10/2017
(Continued)

OTHER PUBLICATIONS

Hairston, Peter, et al., Design of an Instrument for Real-Time Detection of Bioaerosols Using Simultaneous Measurement of Particle Aerodynamic Size and Intrinsic Fluorescence, J Aerosol Sii. Veil. 28. No. 3, pp. 471-482, 1997, Elsevier Science Ltd.
(Continued)

*Primary Examiner* — David P Porta
*Assistant Examiner* — Mamadou Faye
(74) *Attorney, Agent, or Firm* — Timothy E. Siegel Patent Law, PLLC; Timothy E. Siegel

(57) ABSTRACT

A method of detecting bioaerosols, including detecting particles and estimating a particle size for each detected particle and determining a fluorescence strength for each detected particle. Comparing particle size and fluorescence strength for each detected particle to arrive at a normalized fluorescence strength per particle and comparing normalized fluorescence strengths over a time period to a maximum threshold, to detect highly fluorescent manmade substances.

20 Claims, 8 Drawing Sheets

(51) Int. Cl.
*G01N 15/02* (2006.01)
*G01N 15/06* (2006.01)

(56) References Cited

U.S. PATENT DOCUMENTS

| | | | |
|---|---|---|---|
| 4,830,494 | A | 5/1989 | Ishikawa et al. |
| 5,606,170 | A | 2/1997 | Saaski et al. |
| 6,885,440 | B2 | 4/2005 | Silcott et al. |
| 6,967,338 | B1 | 11/2005 | Sickenberger et al. |
| 7,106,442 | B2 | 9/2006 | Silcott et al. |
| 7,375,348 | B1 | 5/2008 | Sickenberger et al. |
| 7,414,720 | B2 * | 8/2008 | Wachtel ............. G01N 15/0205 356/335 |
| 9,500,591 | B1 | 11/2016 | Goad et al. |
| 2003/0098422 | A1 | 5/2003 | Silcott |
| 2005/0247868 | A1 * | 11/2005 | Call ................... G01N 15/0255 250/282 |
| 2006/0232776 | A1 | 10/2006 | Hairston et al. |
| 2006/0237665 | A1 * | 10/2006 | Barney .............. G01N 15/1459 250/458.1 |
| 2006/0238757 | A1 | 10/2006 | Silcott |
| 2006/0250606 | A1 | 11/2006 | Kaye et al. |
| 2009/0222218 | A1 * | 9/2009 | Chamberlin .............. G01J 3/10 702/23 |
| 2010/0261212 | A1 * | 10/2010 | Soman ................... B82Y 15/00 435/21 |
| 2011/0036995 | A1 | 2/2011 | Binnie et al. |
| 2012/0120385 | A1 | 5/2012 | Jiang et al. |
| 2013/0213115 | A1 | 8/2013 | Chu et al. |
| 2013/0286381 | A1 * | 10/2013 | Some ..................... G01N 21/51 356/72 |
| 2015/0168288 | A1 | 6/2015 | Binnie et al. |
| 2015/0276589 | A1 | 10/2015 | Wagner et al. |
| 2017/0241893 | A1 * | 8/2017 | Walls ................. G01N 15/1436 |
| 2017/0268981 | A1 | 9/2017 | Diebold et al. |
| 2018/0024059 | A1 * | 1/2018 | Gouda ............... G01N 21/6486 382/133 |
| 2018/0372609 | A1 | 12/2018 | Wu |

FOREIGN PATENT DOCUMENTS

| | | |
|---|---|---|
| JP | 09273987 | 10/1997 |
| JP | 3204486 | 6/2016 |

OTHER PUBLICATIONS

Healy, David, et al., A laboratory assessment of the Waveband Integrated Bioaerosol Sensor (WIBS-4) using individual samples of pollen and fungal spore material, Department of Chemistry and Environmental Research Institute, University College Cork, Cork, Ireland and Department of Biomedical Engineering, Cork Institute of Technology, Cork, Ireland, Atmospheric Environment 60 (2012) 534-543.

Hill, Steven C. et al, Fluorescence from airborne microparticles: dependence on size, concentration of fluorophores, and illumination intensity, Jun. 20, 2001 / vol. 40, No. 18 / Applied Optics.

Jae Hee Jung et al, Real-Time Fluorescence Measurement of Airborne Bacterial Particles Using an Aerosol Fluorescence Sensor with Dual Ultraviolet- and Visible-Fluorescence Channels, Environmental Sensor System Research Center, Korea Institute of Science and Technology (KIST), Seoul, Republic of Korea, institute of Health and Environment, Graduate School of Public Health, Seoul National University, Seoul, Republic of Korea, Environmental Engineering Science vol. 29, No. 10, 2012.

Kaye, P.H. et al, Single particle multichannel bio-aerosol fluorescence sensor,Science & Technology Research Institute, University of Hertfordshire, Hatfield, Herts. AL10 9AB, U.K and Defence Science & Technology Laboratory, Porton Down, Salisbury, Wilts. SP4 0JQ,, U.K., May 16, 2005 /vol. 13, No. 10 / Optics Express.

Kockelaev, E.A. et al, Study of the angular fluorescence distribution of bioaerosol particles: modelling and experiment, J. Opt. Technol. 79 (6), Jun. 2012.

Pan, Yong-Lee et al., Spectrally-resolved fluorescence cross sections of aerosolized biological live agents and simulants using five excitation wavelengths in a BSL-3 laboratory, Apr. 7, 2014 | vol. 22, No. 7 | DOL10.1364/OE.22.008165 | Optics Express.

Pan, Yong-Lee et al, Using Single-Particle Fluorescence to Detect Bioaerosols, OPN Sep. 2008.

Pinnick, Ronald G. et al, Fluorescence Particle Counter for Detecting Airborne Bacteria and Other Biological Particles, Aerosol Science and Technology 23:653-664 (1995).

Primmerman, Charles A., Detection of Biological Agents, vol. 12. No. 1, 2000 Lincoln Laboratory Journal.

Model 3313 Fluorescence Aerodynamic Particle Sizer Sensor, 2002 by TSI Incorporated.

Sivaprakasam, Vasanthi et al, Spectral characterization of biological aerosol particles using two-wavelength excited laser-induced fluorescence and elastic scattering measurements, Optical Sciences Division, Naval Research Laboratory, 4555 Overlook Avenue S.W., Washington, DC 20375, USA, Mar. 28, 2011/ vol. 19, No. 7 / Optics Express.

Brosseau, Lisa M. et al., Differences in Detected Fluorescence Among Several Bacterial Species Measured with a Direct-Reading Particle Sizer and Fluorescence Detector, Division of Environmental and Occupational Health, University of Minnesota, Minneapolis, MN 55455, 2000 American Association for Aerosol Research.

EPCT Office action PCT Collaborative Search and Examination Pilot Upload peer contribution, Peer ISA—China Intellectual Property.

EPCT Office action PCT Collaborative Search and Examination Pilot Upload peer contribution, Peer ISA—China Intellectual Property, Peer ISA—Japan.

EPCT Office action PCT Collaborative Search and Examination Pilot Upload peer contribution, Peer ISA—China Intellectual Property, Peer ISA—US.

EPCT Office action PCT Collaborative Search and Examination Pilot Upload peer contribution, Peer ISA—China Intellectual Property, Peer ISA—Europe.

International Search Report and Written Opinion of the International Searching Authority for PCT/US19/014596, dated Jun. 14, 2019.

* cited by examiner

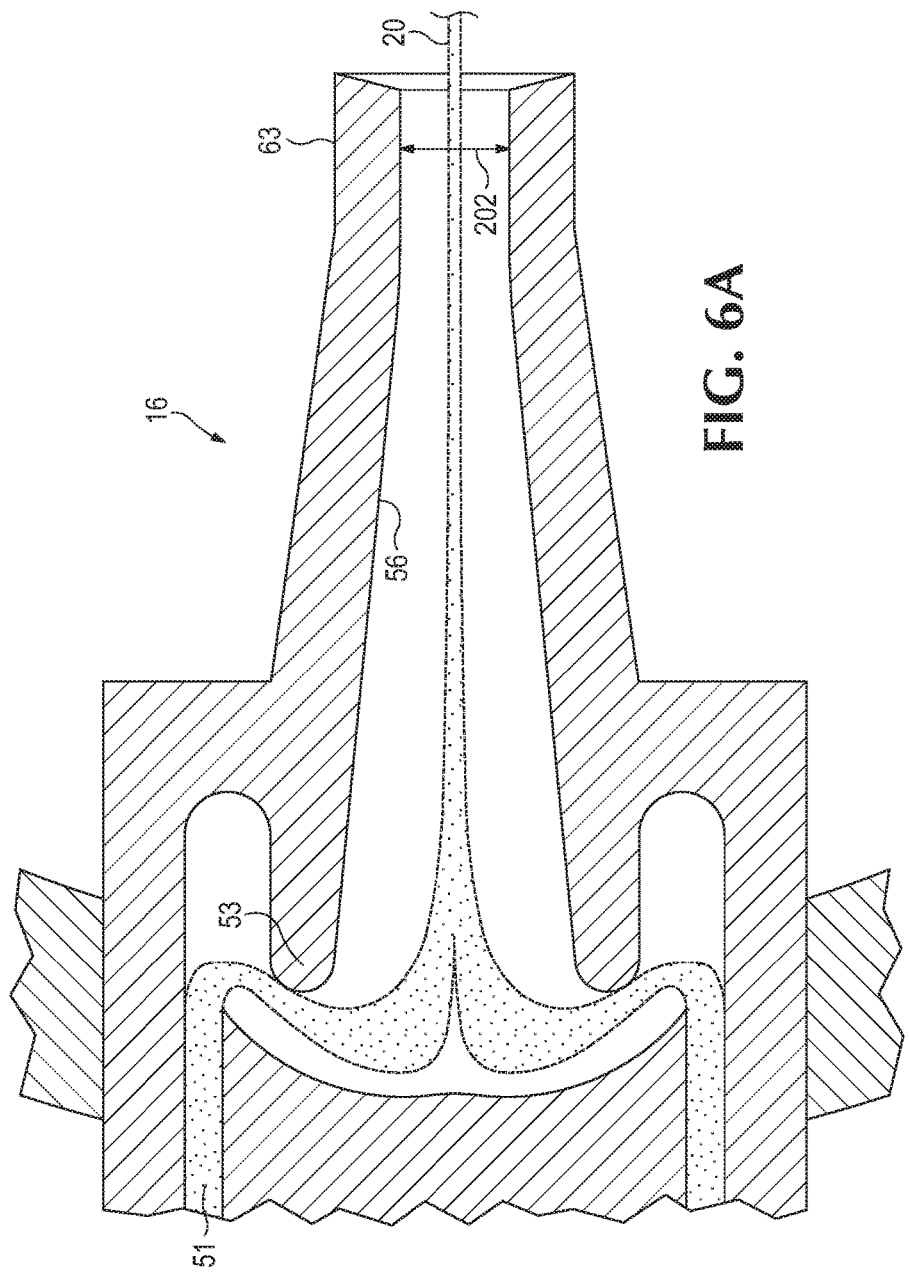

BIOAEROSOL DETECTOR HAVING SAFEGUARDS

RELATED APPLICATIONS

This application claims benefit of provisional application U.S. Ser. No. 62/620,980 filed on Jan. 23, 2018 which is incorporated by reference as if fully set forth herein.

BACKGROUND

There are many situations where it would be desirable to determine biological aerosol levels in surrounding air. Many human, animal and plant pathogens such as viruses and bacteria travel from one host to another either by attachment to an otherwise benign aerosol particle or through a purposeful aerosol lifecycle stage such as a spore. Such bioaerosols are particularly disadvantageous in pharmaceutical manufacturing facilities and clean rooms of any type.

There are a limited number of ways to monitor bioaerosols. The company Proengin of Saint-Cyr-l'École, France markets a product that passes a stream of sampled air through a hydrogen flame. Literature from the company indicates that the spectrometric signature created by oxidation of the bioaerosol can be used to detect many different types of pathogenic organisms. However, it is likely that many carbonaceous materials will present very similar signatures and this approach may be too susceptible to falsely categorize organic aerosols as biological in nature to have much utility except in certain applications.

A second method that has been the subject of considerable research and development, particularly by the U.S. Department of Defense, is based on UV fluorescence. In this approach, advantage is taken of the broad characteristic of organism biochemicals to fluoresce when subjected to ultraviolet light. Fluorescing chemicals are ubiquitous in living organisms, and may be compounds such as aromatic amino acids, NADH, and flavins. In these devices, a stream of air is made to pass through a beam of ultraviolet light (with the light beam usually positioned perpendicularly to the particle beam). Fluorescence emitted from any aerosol particles is then collected optically and converted into a corresponding electronic signal by a photodetector, either particle-by-particle or in an ensemble integrated mode. In both cases an electronic signal is generated that is proportional to the local bioaerosol concentration.

This has advantages over the flame photometry approach in that it is likely to have less false positives from atmospheric organic debris, there are no consumables, and highly flammable hydrogen is not needed. In addition, differences in fluorescence intensity may help discriminate against some natural or manmade organic aerosol particles that are not of interest. A particle-by-particle approach is preferred because it allows a more detailed examination of aerosol composition, but the intensity of fluorescent light emitted by a single bioaerosol particle is very small, generally only $\frac{1}{1000}$ or less the intensity of light scattered by the particle. Hence, highly efficient methods of collection and electro-optic conversion are required.

Preferred detection devices are the photomultiplier tube (PMT) and avalanche photodiode. The PMT has very high gain but may be somewhat bulky and fragile, while solid state devices such as the avalanche photodiode can be quite small but have less gain and may not be capable of operation at higher temperatures. Which approach is more suitable depends on the application.

At first glance, it would seem desirable to design the excitation optics and air stream injector so that each particle's fluorescence signature is maximized. This has been the approach most often used in aerosol particle sizing devices. Particles are forced through an aperture and made to pass through the focused beam from a laser diode. This produces a large photon pulse which is converted to an equivalent electronic pulse by the detector. These pulses are then summed, and the sampled concentration calculated based on the known air flow. One disadvantage of this analog approach is that there is no way to know how many of the counts are truly associated with particle transits as opposed to background noise pulses (such as generated internally by the detector) without halting the sampling process and measuring the background count rate. This would be extra work for an operator and force a period of time when no sampling was being performed.

There may also be a tradeoff between maximizing the fluorescence signature of particles that are detected, and the uniform detection of a significant proportion of particles in the air stream. For example, the image spot size from a solid state laser may be made very small and the local light intensity very high so that particles passing through the focal point will be intensely excited. It is exceedingly difficult, however, to focus an air stream containing 1 to 10 micron particles to a correspondingly small cross-section. In typical embodiments either only a fraction of the particles in the air stream pass through the laser beam's focal point and many particles sampled by the measuring device pass through undetected, or the particles are forced to pass through such a small aperture that there is a risk of the aperture clogging over time. In addition, the radial intensity distribution around the propagation axis of a laser beam is typically Gaussian and particles passing at different distances from the focal point would see varying levels of UV excitation, making it very difficult to quantitatively estimate the overall aerosol sample's particle size distribution.

Essentially all bioaerosol detectors reported in the literature or sold on the market use mirror optics to collect and focus signal fluorescence onto a photodetector. This is due in part to a lack of low-cost refractive optics at ultraviolet wavelengths and to a preference on the part of those knowledgeable in the art to use metal reflective optics since, to the first order, they are insensitive to the working wavelength. Also, the curved mirrors used are focused on the intersection of the light beam and air stream, thereby maximizing the reflection of the faint fluorescent signals created. This may, however create a large expense in system manufacture and maintenance, as the reflective optic components can be quite costly and are very difficult to clean without damaging the reflective surface.

SUMMARY

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

In a first separate aspect, the present invention may take the form of a bioaerosol detector, including a housing defining a chamber and an air stream injection assembly, producing an airstream with entrained particles having an average velocity within a transverse extent, in the chamber. Further, a light source produces a light beam that intersects the air stream and a light detection assembly is configured and positioned to detect light generated by scattering of light from the light beam, by particles in the air stream. Also, a digitizer produces a sequence of first digital values, representative of light detection, responsive to the light detection assembly. Finally, a data processor repeatedly calculates a background noise level, responsive to the sequence of first digital values, which is responsive to a high density of small particles condition wherein the noise level rises due to small particles in the air stream that are not detected and are sufficiently numerous to raise the noise level, thereby obscuring the particles from detection, by detecting a condition in which the noise level has risen above a threshold.

In a second separate aspect, the present invention may take the form of a bioaerosol detector, including a housing defining a chamber and an air stream injection assembly, producing an airstream with entrained particles having an average velocity within a transverse extent, in the chamber. Further, a light source produces a light beam that intersects with and has a minimum transverse extent equal to or greater than the air stream's transverse extent and a photon detection assembly includes an optical train and a photon detector and is configured and positioned to generate an output pulse in response to a photon encounter, from light emitted from the light source and scattered by a particle in the air stream. A digitizer is responsive to the photon detector, to produce a sequence of first digital values, each first digital value representing detections of output pulses from the photon detection assembly, per a unit of time duration. Finally, a photon detector continuous high state sensor is also responsive to the photon detection assembly, and is adapted to detect a continuous high output state, thereby indicating that a flood of photons is preventing the photon detector from transitioning into a low state between photon encounters.

In a third separate aspect, the present invention may take the form of a particle detector, including a housing defining a chamber, an air stream injection assembly, producing an airstream, having a transverse extent, in the chamber and a light source, producing a light beam that intersects with the air stream. Further, a light detection assembly is configured and positioned to detect scattering of light from the light beam, by particles in the air stream and a digitizer is responsive to the light detection assembly, to produce a sequence of first digital values, each first digital value representing light detected per a unit of time duration. Finally, a data processing assembly computes a background noise estimation, responsive to the sequence of digital values, and repeatedly determines if interior surfaces of the light detection assembly have become degraded by adherent particles, by analyzing changes to the background noise estimation over time to determine if an increase in background noise above a background noise increase threshold has taken place over a time period longer than a time period threshold.

In a fourth separate aspect, the present invention may take the form of a method of detecting bioaerosols, including detecting particles and estimating a particle size for each detected particle and determining a fluorescence strength for each detected particle. Comparing particle size and fluorescence strength for each detected particle to arrive at a normalized fluorescence strength per particle and comparing normalized fluorescence strengths over a time period to a maximum threshold, to detect highly fluorescent manmade substances.

In a fifth separate aspect, the present invention may take the form of a bioaerosol detector including a housing defining a chamber, an air stream injection assembly, producing an airstream with entrained particles having an average velocity within a transverse extent, in the chamber and an ultraviolet light source, producing a light beam that intersects the air stream. Also, a scattering light detection assembly is configured and positioned to detect light generated by scattering of light from the light beam, by particles in the air stream, and includes a first lens that has a surface facing the chamber and a fluorescence light detection assembly, includes a long wavelength filter, and detects longer wavelength light indicative of light that has been created by biofluorescence, from the particles in the air stream, and includes a second lens that has a surface facing the chamber. Finally, the scattering light detection assembly can be removed as a single unit, thereby permitting easy access to the first lens, to permit cleaning of the lens.

In addition to the exemplary aspects and embodiments described above, further aspects and embodiments will become apparent by reference to the drawings and by study of the following detailed descriptions.

BRIEF DESCRIPTIONS OF THE DRAWINGS

Exemplary embodiments are illustrated in referenced drawings. It is intended that the embodiments and figures disclosed herein are to be considered illustrative rather than restrictive.

FIG. 6A is a cross-sectional view of a sampled air injection nozzle that shifts sampled particles away from the nozzle walls.

DESCRIPTION OF PREFERRED EMBODIMENTS

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Preferred Embodiment System Overview

Figure 1:
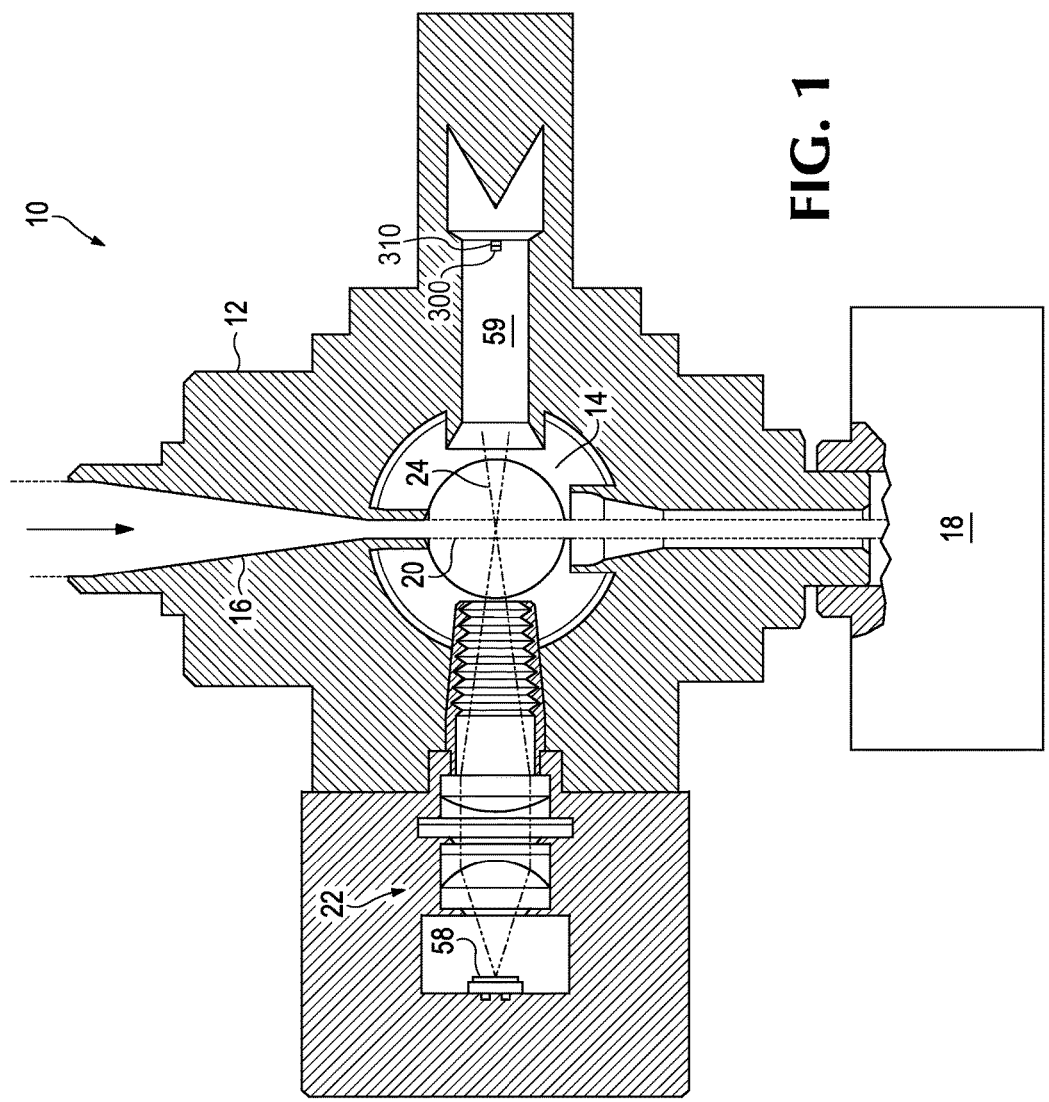
FIG. 1 is a sectional view of bioaerosol detector according to the present invention.

Referring to FIG. 1, in a preferred embodiment of a bioaerosol detector 10 (which may also be termed a "particle detector"), a housing 12 defines a chamber 14. An air nozzle assembly 16, and a centrifugal air pump 18 (which may collectively be termed an "air stream injection assembly"), create an air stream 20 having a constant flow rate. Also, a light source optical train 22 (which may be referred to simply as a "light source"), creates an ultraviolet (UV) fluorescence-stimulating light beam 24 at a 90-degree angle to air stream 20, such that light beam 24 and air stream 20 intersect orthogonally creating a cylinder-shaped illuminated segment of the air stream 20 at the geometric center of the chamber 14.

Figure 2:
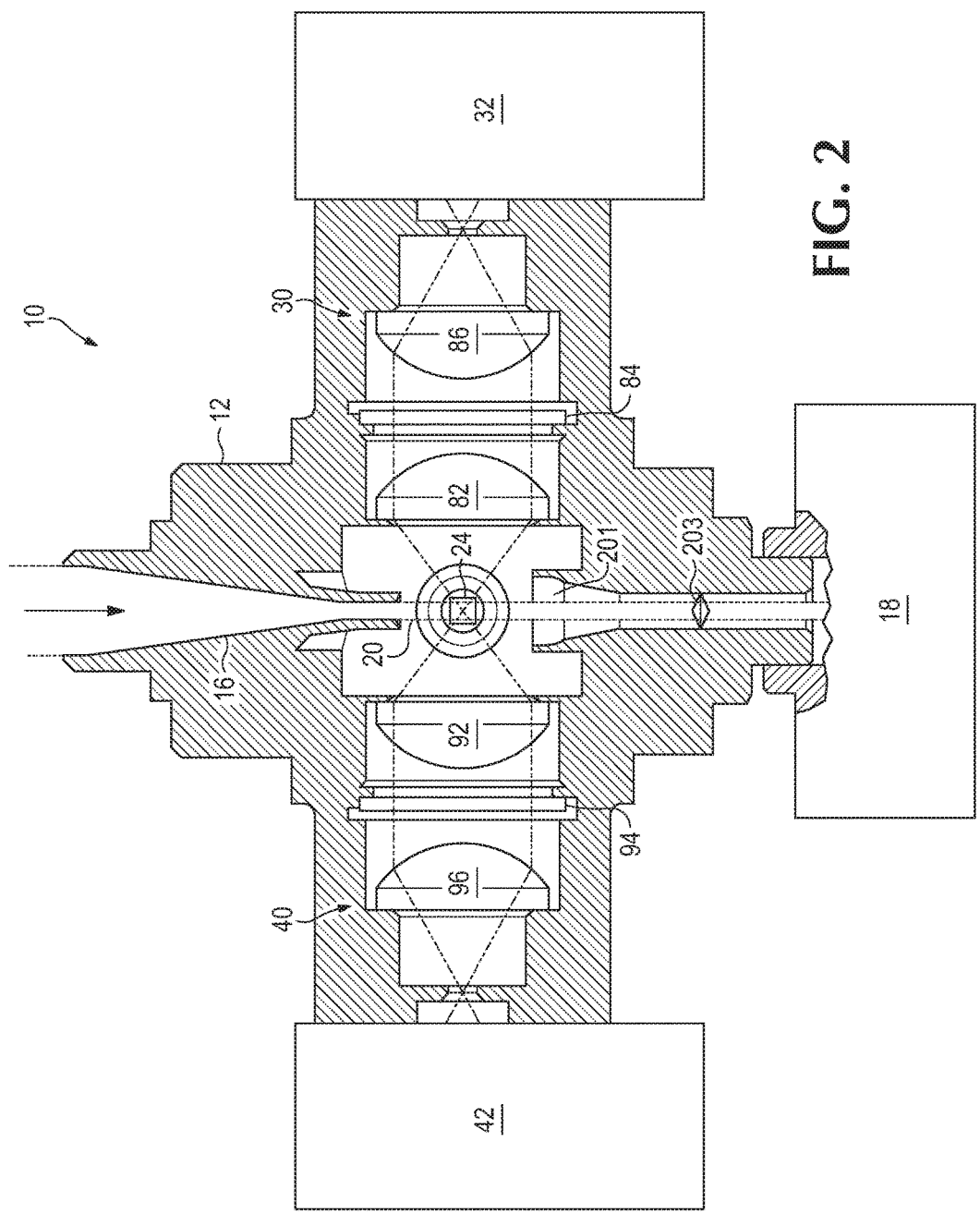
FIG. 2 is a sectional view of the bioaerosol detector of FIG. 1, taken at a 90-degree angle to the sectional view of FIG. 1.

Referring now to FIG. 2, a fluorescence photon detection optical train 30 and a scattering photon detection optical train 40 (which may be referred to, singly or collectively, as a "light detection assembly"), discussed in greater detail further on, are placed on a common centerline that is preferably located at 90 degrees to the plane defined by the air stream 20 and light beam 24 centerlines. Fluorescence detection train 30 is long-pass filtered to permit the detection of light that has been emitted by fluorescent organic substances, which will be shifted to longer wavelengths relative to the waveband that is characteristic of light source optical train 22 (FIG. 1), whereas scattering detection train 40 is short-pass filtered to detect scattering from particles, which should be about 3 orders of magnitude, or more, greater in strength than the fluorescence signal. Trains 30 and 40 conclude with a fluorescent photon-counting multiplier tube (PMT) 32 and a scattering PMT 42, respectively.

Figure 3:
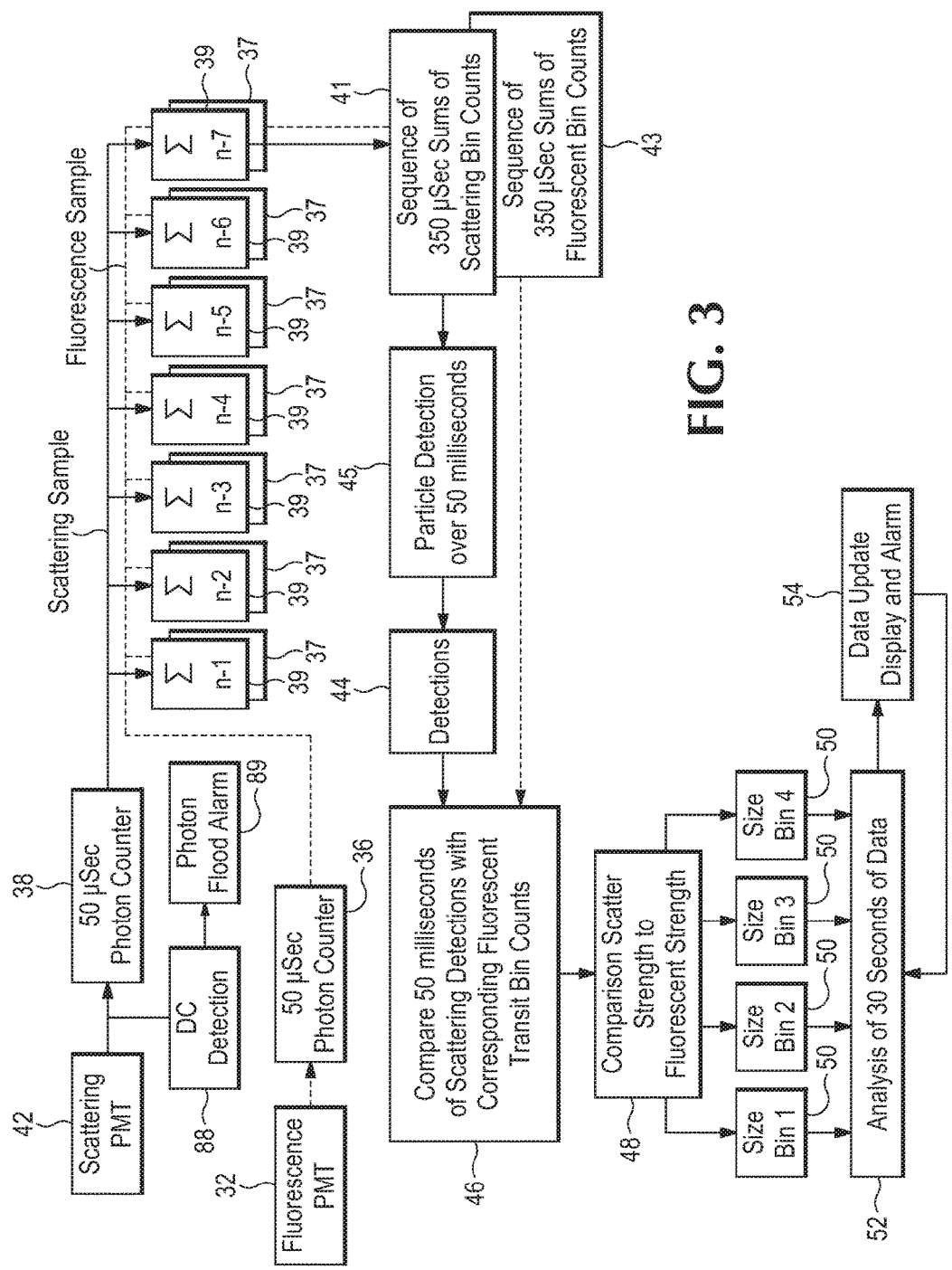
FIG. 3 is a block diagram describing the processing of data gathered from the system of FIG. 1.

As a non-limiting example with reference to FIG. 3, the traversal time of a particle passing through the light beam 24 is 350 µSecs. To obtain a robust signature of the particle's travel through the beam, overlapping 350 µSec scattering and florescent transit bin counts 41 and 43, respectively, are iteratively summed from 50 µSec intervals of photon counts (which may also be referred to as "digital values") collected by counters 38 and 36 (which may also be referred to as "digitizers"), respectively, from PMTs 32 and 42, respectively. Although the following discussion continues with 50 µSec counts, collected by counters 38 and 36, other initial counts, typically between 25 µSec and 60 µSec are used in alternative preferred embodiments. The overlapping 350 µSec periods will be termed "transit bin periods," and the summed photon counts over these periods will be termed "transit bin counts" or "summed digital values". The transit bin periods are incremented every 50 µSecs, so that they overlap by 300 µSecs, with nearest neighbor transit bin periods. As it takes 350 µSec for a particle to traverse the light beam, there will always be a transit bin period (having a count 41) that is offset by less than 25 µSecs, for each particle traversal of the light beam. Particle detection 45 and particle size estimation is performed using an array of scattering transit bin counts 41, collected over about 50 milliseconds. For every particle detected 44, a size bin 50, corresponding to a particle size range is incremented by one, thereby keeping a tally of the number of detections of particles in that range of sizes. Then the corresponding fluorescent transit bin counts are selected (block 46) and compared ratiometrically to net scattering transit bin values (block 48), with the resulting ratio (normalized value of fluorescence) also assigned to a size bin 50, to keep a running tally of the fluorescence-to-scattering ratio.

To characterize aerosols affecting human or animal health, the number of bins may typically be from one to eight, with four bins usually being sufficient for detailed examination without requiring excessive computational capabilities or creating objectionable statistical noise in the individual transit bin counts. When a potentially dangerous condition is detected, an alarm is sounded 54. Every thirty seconds, the final data results are evaluated 52 and made available 54 for review by a user, including:
  Concentration of aerosol particles in the airstream for each size bin range
  Percentage of aerosol particles that are biological in nature for each size bin
  Scaled fluorescence intensity for each particle size bin
  Background fluorescence and scattering levels Light Beam and Air Stream Referring to FIG. 1, the UV light beam 24 is produced by a long-lived high-power UV LED 58, such as the NCSU033b, manufactured by Nichia Corporation of Tokushima, Japan and operating nominally at 365 nm, having a 1 mm×1 mm emitting face, over which area light is emitted very evenly. In preferred embodiments, LED 58 emits light evenly over a face having an area greater than 0.5 mm$^2$. This light is focused by a light source optical train 22 so that the LED's emitting face is imaged onto a plane that is coincident with both the photon detection and air stream 20 centerlines. A design objective for UV light intensity over the air stream 20 cross-section (See FIG. 4, 20; FIG. 5, 24) is that the light intensity varies by 25% or less. This is difficult to achieve with a solid-state laser diode, for example, as the source is very small, may be anisotropic in emission pattern, and is typically nonuniform in intensity over its cross-section. In a preferred embodiment, optical train 22 projects light beam 24 such that it is magnified by a factor of 1.5×, at the intersection with the air stream 20. In another preferred embodiment, this ratio is 2×. Typically, this ratio may range from 1.0× to 2.5×. In preferred embodiments, light beam 24 is square in cross-section and has dimensions of greater than 0.75 mm by 0.75 mm at its intersection with air stream 20. In preferred embodiments, air stream 20 is round in cross-section and has a diameter of greater than 0.5 mm and less than 2 mm. In preferred embodiments, particles entrained in air stream 20 take more than 80 µSecs and 800 µSecs to transit light beam 24.

Light that is not deflected by a particle traverses chamber 14 into a light dump 59 to minimize stray light reaching the detectors. Light dump 59 may incorporate a fiber optic link 310 and photodetector 300, or any alternative method for monitoring the output of UV LED 58 that does not disturb the excitation process or the function of light dump 59. Photodetector 300 can be used to detect LED failure or to provide a reference signal for ratiometrically correcting for any decay in excitation light intensity over time.

Figure 4:
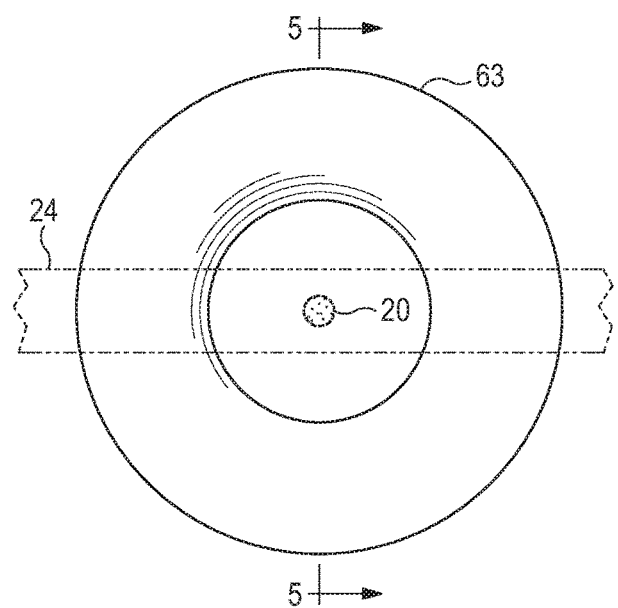
FIG. 4 is a detail view of the intersection of the light beam with the sampled air stream, occurring at the center of the sectional view of FIG. 1.
Figure 5:
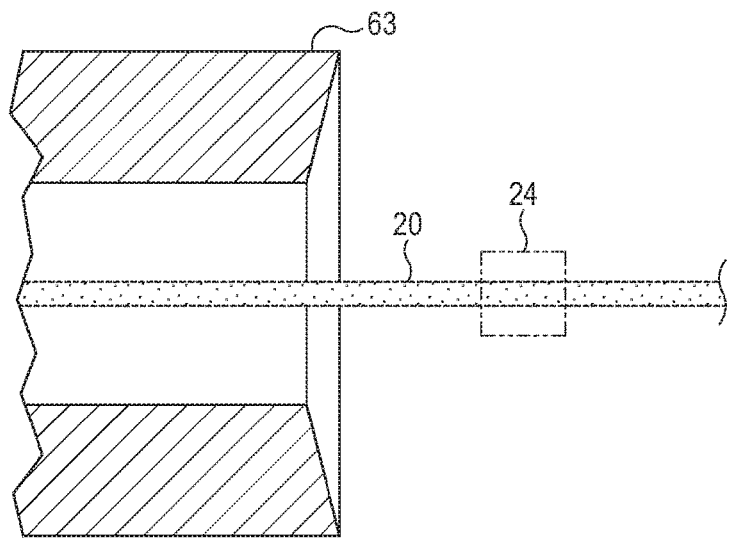
FIG. 5 is a detail view of the intersection shown in FIG. 4, shown along view line 5-5 of FIG. 4.

FIGS. 4 and 5 depict detail views of the intersection of the light beam 24 with the sampled air stream 20, occurring at the center of the sectional view of FIG. 1. Note that the circular side wall 63 of the nozzle 16 has not been drawn to scale with regard to the cross section of the light beam 24 and air stream 20. Thus, the nozzle may not be positioned as close to the cross section of the light beam 24 and air stream 20. Rather, the scale of FIGS. 4 and 5 is for effect, to highlight that the focused light beam 24, has preferably straight, parallel edges where the air stream 20 intersects with it and has an equal or greater minimum height and width than the air stream 20, which typically has a cylindrically symmetric concentration profile. Hence, if the focused LED image is 1.5 mm square (a 1.5× magnification ratio for a 1 mm square emitting area), then the particle beam diameter must not exceed 1.5 mm. Accordingly, when this criterion is met, every particle in the air stream 20 travels the same distance across light beam 24, and, as the air stream's speed is very even over its transverse dimension, spends the same dwell time in light beam 24. As the light beam 24 is equally bright over its transverse extent, each particle is illuminated with the same amount of light as it transits the light beam 24. An equally important feature is that the air stream and light beam cross-sections at intersection are much larger than the cross-sections of the particles being examined, preferably on the order of 100 times or more, making the likelihood of the air stream inlet orifice clogging very low. Clogging may also be prevented by the use of various upstream filters or screens that remove larger particles and floating debris from sampled air.

Air stream 20 may be formed using a conventional converging nozzle assembly 16 as shown in FIGS. 1 and 2. A disadvantage of this approach is that there may be some tendency for aerosol particles to impact on and adhere to the converging portion of the nozzle. However, this is generally self-limiting to formation of a monolayer of aerosol debris on that surface. An issue of more concern is that the axial velocity of air stream 20 may decrease too rapidly as the nozzle wall is approached, resulting in particles at nozzle exit having too large a range of velocities.

This may be counteracted by having the air stream 20 generate centrifugal forces that move entrained particles in the desired size range away from the nozzle wall. To achieve a more constant air velocity in air stream 20 and to move particles away from the nozzle walls, referring to FIG. 6A, a preferred air nozzle assembly 16 includes an annular air intake 51, open to ambient air outside of detector 10, and a circular baffle structure 53 which redirects sampled air through an S-shaped radially inward directed path, causing it to accelerate as it heads towards nozzle throat 56, where it is accelerated further by the narrowing passageway 56. A centrifugal air pump 18 (FIG. 1) is used to draw air through chamber 14, and thereby, through nozzle assembly 16. Air stream 20 emerges from air nozzle assembly 16 with a nominally flat velocity profile across about 80% of the nozzle exit diameter and with entrained particles shifted away from the nozzle's interior walls. This particle behavior is induced by making the nozzle relatively short in order to prevent emergence of a fully developed flow profile. Centrifugal forces created by the S-shaped radially inward air flow cause entrained aerosol particles that are initially close to the exterior nozzle wall to be shifted towards the center of the flow and away from the wall. This causes fewer particles to be lost through wall adhesion prior to entering the interrogation chamber 14 as well as ensuring that entrained particles reside in a more centrally located cross-section of the sampled air flow where the velocity is more constant in value. A design criterion is that air velocity (and hence particle velocity) not deviate by more than 20% from an average value over the area defined by the aerosol stream's maximum outside diameter projected onto the plane defined by the excitation and detection optics axis'.

The Reynold's number of the air flow 20 is maintained in the laminar or transitional range to minimize turbulence in chamber 14. In one preferred embodiment, the sampled air flow is 1.2 liters/minute, the annular air intake 51 has a width of 1 mm and an outside diameter of 7.4 mm and the nozzle exit diameter 202 is 1.5 mm (See FIG. 6A). In a second preferred embodiment, the air flow may range from 0.25 to 3 liters/minute. To minimize radial expansion of the particle beam after it exits the nozzle assembly 16, in any preferred embodiment the air stream 20 exits into a collection nozzle 201 (FIG. 2) that has a minimum flow diameter 203 that is substantially the same as exit diameter 202 (FIG. 6A) of nozzle assembly 16.

Figure 6B:
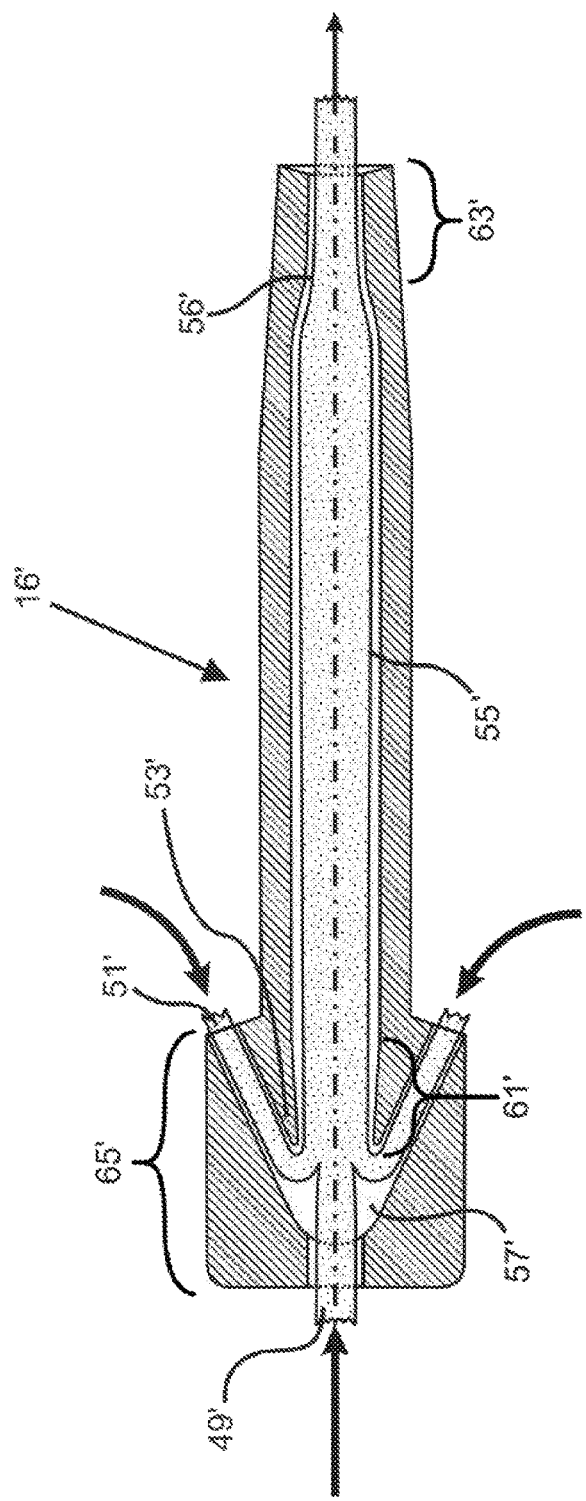
FIG. 6B is a cross-sectional view of a second sampled air injection nozzle having a smaller profile relative to the air injection nozzle of FIG. 6A, while still shifting sample particles away from the nozzle walls.

In some situations, there may not be enough physical space to accommodate nozzle assembly 16's S-shaped aerosol deflecting structure, or the nozzle exterior may obstruct too much signal light. Another preferred embodiment to prevent aerosols from contacting the nozzle interior walls is shown in FIG. 6B. In this approach, a cone-shaped channel 51' extends from the exterior of a cylindrical inlet section 65' to a radially symmetric interior volume 57'. The interior volume 57' communicates with the interrogation chamber 14 through a coaxial expansion section 61' and cylindrical extension tube 55'. Intersection of the cylindrically symmetric cone-shaped channel 51' with the interior volume 57' causes a lip 53' to be formed at the interior volume 57' discharge face.

As sampled air flows radially inward through the conic channel 51', those streamlines that enter and pass near to the lip 53' are strongly curved and exert a centrifugal force on entrained aerosol particles in said stream flow. This centrifugal force urges said particles to move away from the wall of expansion section 61' and cylindrical extension tube 55'. Correspondingly, as the airflow enters the interior nozzle 63', there is an annular zone of flow adjacent to the nozzle interior wall 56' that is significantly reduced in respirable aerosol particles that are of the order of 1 micron in size, or greater.

Optionally, a second tubular sampled air inlet 49' may be added that coaxially penetrates to the cylinder's interior volume 57' from the end of the volume 57' that is opposite the expansion section 61'. While this second air inlet has a negligible effect on particle contact with the nozzle interior wall, it is effective at stabilizing the air flow exiting the interior volume 57' and entraining large particles. In the absence of this secondary inlet flow, larger particles may tend to impact the walls of the interior volume 57'.

The conic channel 51' may have a width of 0.5 to 0.75 mm; the cone channel's angle relative to the axis of inlet section 65' may range from 5 to 30 degrees, and the radius of curvature of the lip 53' shall be less than 0.5 mm. The lip diameter shall be 2 mm, the expansion angle less than 5 degrees, the extension tube diameter 2.5 mm, and the nozzle exit diameter shall be 1.5 mm. If the second air inlet is employed, the diameter may usefully range from 0.5 mm to 2.mm and the percentage of airflow through the secondary inlet 49' may range from 5% to 25%. In one embodiment, dependent on the setting of the centrifugal air pump, the air stream exiting the nozzle (FIG. 6B), may have an average velocity of about 1500 cm/sec and a dwell time of only 100/μSec. In a second embodiment the average exiting air stream velocity may be 430 cm/sec. This velocity yields a 350 μSec dwell time of entrained particles in the 1.5 mm square light beam 24.

As with the other aerosol deflecting structure, it is desirable to operate either in laminar or transitional flow and to avoid turbulence, as turbulence will encourage transport of aerosol particles towards the inlet nozzle walls.

Scattering and Fluorescence Optical Pathways

As seen in FIG. 2, optical train 30 begins with a fluorescence-train collection lens 82 and optical train 40 begins with a scattering train collection lens 92. Both lenses 82 and 92 have an object point at the intersection of air stream 20 and light beam 24 that coincides with the lens's focal length.

Collected light emerges from each collection lens 82 and 92 in a nominally collimated condition, that is, the light rays are parallel to the lens centerline. Such collimated rays are amenable to wavelength filtering using dichroic filters consisting of multilayer films that can be constructed to pass either short wavelengths of light or long wavelengths (short pass and long pass filters, respectively). Accordingly, the light from lens 82 encounters long pass dichroic filter 84 and the light from lens 92 encounters short pass dichroic filter 94. Both filters are aligned perpendicular to the respective lens axis. Long pass filter 84 passes the light resulting from the fluorescence of fluorescent organic substances, which produces longer wavelength light than the light that illuminates the biological substances. The shorter wavelength light is reflected by filter 84. In similar manner, light that is at the wavelength emitted by light source train 22 (FIG. 1) is passed by short pass filter 94, and longer wavelength light is reflected.

The reflected light from filters 84 and 94 is focused by lenses 82 and 92, respectively to the chamber 14 (FIG. 1) center, from which point it travels through the lens 92 or 82, respectively (unless the particle from which the light was reflected is directly in the center, in which case it partially blocks this light). In this manner, fluorescent light that is reflected from short pass filter 94 is then redirected to the fluorescent detection optical train 30 and light that is reflected from long pass filter 84 is redirected to scattering detection optical train 40, in both cases, adding to the detected signal.

The light passing through filters 84 and 94 is focused by lenses 86 and 96, respectively, to detection surfaces of photon-counting multiplier tubes (PMTs) 32 or 42, respectively, where photons are counted and stored in a sequence of consecutive sampling time bins.

In a preferred embodiment, to minimize certain aberrations and reduce manufacturing cost, lenses 82, 86, 92 and 96 are of the same design. These lenses are preferably plano-convex, with the convex profile being aspheric to maximize light capture. Further the refractive index of theses lenses is substantially the same for the scattering and fluorescent light, and the surfaces are anti-reflection coated to minimize Fresnel reflections. Further, the antireflection coatings are very durable and protect the underlying glass, thereby making the lenses amenable to cleaning.

To minimize the effect of refractive index variations, if there is substantive separation of the scattering and fluorescence channel (30 and 40) spectral pass bands, it is preferable to use a focal length for the light capturing lenses 82 and 92, that is characteristic of a wavelength midway between the excitation and fluorescence channel pass bands. But a wavelength midway in each respective channel pass band is recommended for the second lenses 86 and 96 that transfer signal light to the respective photodetectors 32 or 42. Depending on the scattering and fluorescence channel (30 and 40) pass bands, one out of a number of low self-fluorescing optical glasses is used. In one variant this glass is fused quartz.

Starting with blocks 39 and 37, actions shown in FIG. 3 are performed by a computer, in one embodiment in the form of a dedicated computer that is connected to the portions of the detector 10 shown in FIGS. 1 and 2, for example a laptop computer connected by a USB cable and having a display or an auditory warning system, or both (more broadly a "human perceptible notification device") for informing a user of alarm conditions (noted below) and a keyboard for user input. In an alternative preferred embodiment, the computer is in the form of a microprocessor/microcontroller with associated random-access memory and static memory (for storing computer instructions) which is integrated into the portions of detector 10 shown in FIGS. 1 and 2, together with a display and user data input device.

Data Processing and Detection
Computation of Transit Bin Counts

As noted in the overview, sampling counters 36 and 38 deliver values of the number of photons (which may also be referred to as "first digital values") received by the PMTs over a collection time that typically is ⅓ or less of the particle transit time. In a preferred embodiment, these values are delivered to a microprocessor (not shown) for further processing, as shown in FIG. 3 and described below. In an alternative preferred embodiment, a laptop or tablet computer is connected to detector 10, by a USB cable or other means, and has an installed program to perform the processing described below. In the embodiment in which a microprocessor is used, a display and keyboard (not shown) may be connected to the microprocessor, to permit a human user to input choices and to be advised of alarm conditions and other data.

As noted previously, in one preferred embodiment it takes a particle 350 μSecs to pass through the light beam 24. If consecutive 350 μSec time intervals were used for detection, a particle that was evenly split in its transit time between time intervals would in this worst case appear at half its actual count strength in either interval. Both particle arrival time and photon emission follow Poisson statistics: To obtain maximum accuracy in determining each particle's optical output, it is desirable for the majority of photons emitted by any single particle to reside in a single transit time bin. To avoid these issues, the preferable transit bin period should be about 75% or more of the actual particle transit time, and counters 36 and 38 should accumulate counts for coincident time periods that are not more than about ½ of the transit bin's period. In the nonlimiting example, where the counters" 36 and 38 sampling period is 50 μSecs, the sampling period and time shift are ⅐ of the transit bin period.

Any transit bin period that exceeds the actual particle transit time will trap all photons emitted during transit, but an excessively large transit bin period may begin to affect the device's ability to distinguish between particles that are closely spaced in time, that is, when the sampled particle concentration is high. Accurately determining background noise levels also becomes more difficult. For that reason, transit bin periods that are greater than about 2 times the actual particle transit time are not suitable except when sampled particle concentrations are known to be low.

Transit Bin Count Accumulation Method

In a preferred embodiment, 50 μSec samples are formed, with each sample sequentially added to each one of seven, different transit bin summing locations 39 (collectively, a "summing assembly"), to form a part of 7 different overlapping 350 μsecond sampling interval sums. Table 1 illustrates this process over a span of 18 sampling periods, that is, an elapsed time of 900 μSecs. Note that the first 6 transit bin counts are short-counts and unusable. If the total elapsed time represented by the transit bin data array is significantly greater than the transit time, the loss of these data points is not a material issue.

TABLE 1

Example transit bin period correlation with a 350 µSec Transit Bin period and a 50 µSec Sampling Bin period)

| Transit bin | 50 µSecs time increments → | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| 1 | 1 | | | | | | | | | | | | | | | | | |
| 2 | 2 | 1 | | | | | | | | | | | | | | | | |
| 3 | 3 | 2 | 1 | | | | | | | | | | | | | | | |
| 4 | 4 | 3 | 2 | 1 | | | | | | | | | | | | | | |
| 5 | 5 | 4 | 3 | 2 | 1 | | | | | | | | | | | | | |
| 6 | 6 | 5 | 4 | 3 | 2 | 1 | | | | | | | | | | | | |
| 7 | 7 | 6 | 5 | 4 | 3 | 2 | 1 | | | | | | | | | | | |
| 8 | | 7 | 6 | 5 | 4 | 3 | 2 | 1 | | | | | | | | | | |
| 9 | | | 7 | 6 | 5 | 4 | 3 | 2 | 1 | | | | | | | | | |
| 10 | | | | 7 | 6 | 5 | 4 | 3 | 2 | 1 | | | | | | | | |
| 11 | | | | | 7 | 6 | 5 | 4 | 3 | 2 | 1 | | | | | | | |
| 12 | | | | | | 7 | 6 | 5 | 4 | 3 | 2 | 1 | | | | | | |
| 13 | | | | | | | 7 | 6 | 5 | 4 | 3 | 2 | 1 | | | | | |
| 14 | | | | | | | | 7 | 6 | 5 | 4 | 3 | 2 | 1 | | | | |
| 15 | | | | | | | | | 7 | 6 | 5 | 4 | 3 | 2 | 1 | | | |
| 16 | | | | | | | | | | 7 | 6 | 5 | 4 | 3 | 2 | 1 | | |
| 17 | | | | | | | | | | | 7 | 6 | 5 | 4 | 3 | 2 | 1 | |
| 18 | | | | | | | | | | | | 7 | 6 | 5 | 4 | 3 | 2 | 1 |

(each Transit Time Bin correlation is the sum of 7 small bins)
(Each new correlation is shifted 50 us in time)

In this method, summing locations 39 (FIG. 3) are initially set to zero. Then, over the next 350 µSec, the values from scatter channel counter 38 are sequentially stored in the first 7 consecutive memory locations. After another 50 µSec, the counter 38 values are added to 7 consecutive memory locations; but the first memory location has been incremented by one location, relative to the initial step. Accordingly:

1. The first 50 µSec scattering count goes in summing locations 1,2,3,4,5,6, and 7
2. The second 50 µSec scattering count is added to summing locations 2,3,4,5,6,7, and 8
3. The third 50 µSec scattering count is added to summing locations 3,4,5,6,7,8, and 9
4. Further iteration.

This can be easily implemented with both counters 38 and 36. In a preferred embodiment only the scatter channel values are used to detect particles since scattering photon count rates are typically a few orders of magnitude higher than fluorescent photon count rates, so the photons that are scattered from a particle are far easier to distinguish over a noise floor than are the photons produced by fluorescence. Each transit bin that best matches the time period over which a particle traversed the light beam will exhibit a local maximum in bin counts and those specific scattering and fluorescent transit bins provide the scattering and fluorescence information necessary to characterize the sampled aerosol environment. Using the information contained in these transit time bin arrays, a number of useful factors can be determined from the fluorescent photon and scattering photon signatures recorded by PMTs 32 and 42 including most importantly, net scattering and fluorescence photon counts on a particle-by-particle basis. Various peak-finding algorithms can be employed to search out and identify these local maxima, and standard statistical tests can be used to ensure that they are not random peaks attributable to background noise.

In a preferred embodiment, the processes of fluorescent and scattering transit bin accumulation are automated and implemented as direct memory access (DMA) procedures. This saves processor time, which can then be used to analyze long arrays of transit bin counts. Also, as the process is firmware implemented, it can be changed in firmware, yielding greater flexibility in development and use.

Algorithms for Determining Mean Noise and Standard Deviation

A significant advantage of this invention is the ability to calculate system background noise in real-time. Conventional analog pulse methods where each received electronic pulse is assumed to represent a particle transit are fundamentally flawed in that many of the received counts may be attributable to system noise. The only way to determine the background count in such analog systems is to cease sampling and determine the background count rate empirically. This is not satisfactory as an important event may occur during this dead time. Here, background noise calculations are performed for both channels while peak (particle crossing) detection is performed using the scatter channel transit bin counts 41. Background noise count rates are important since they can be subtracted from gross count rates to determine net photon counts attributable to each particle's scattering and fluorescence transit signatures. Also, they are a factor in setting a threshold for particle detection.

Figure 7:
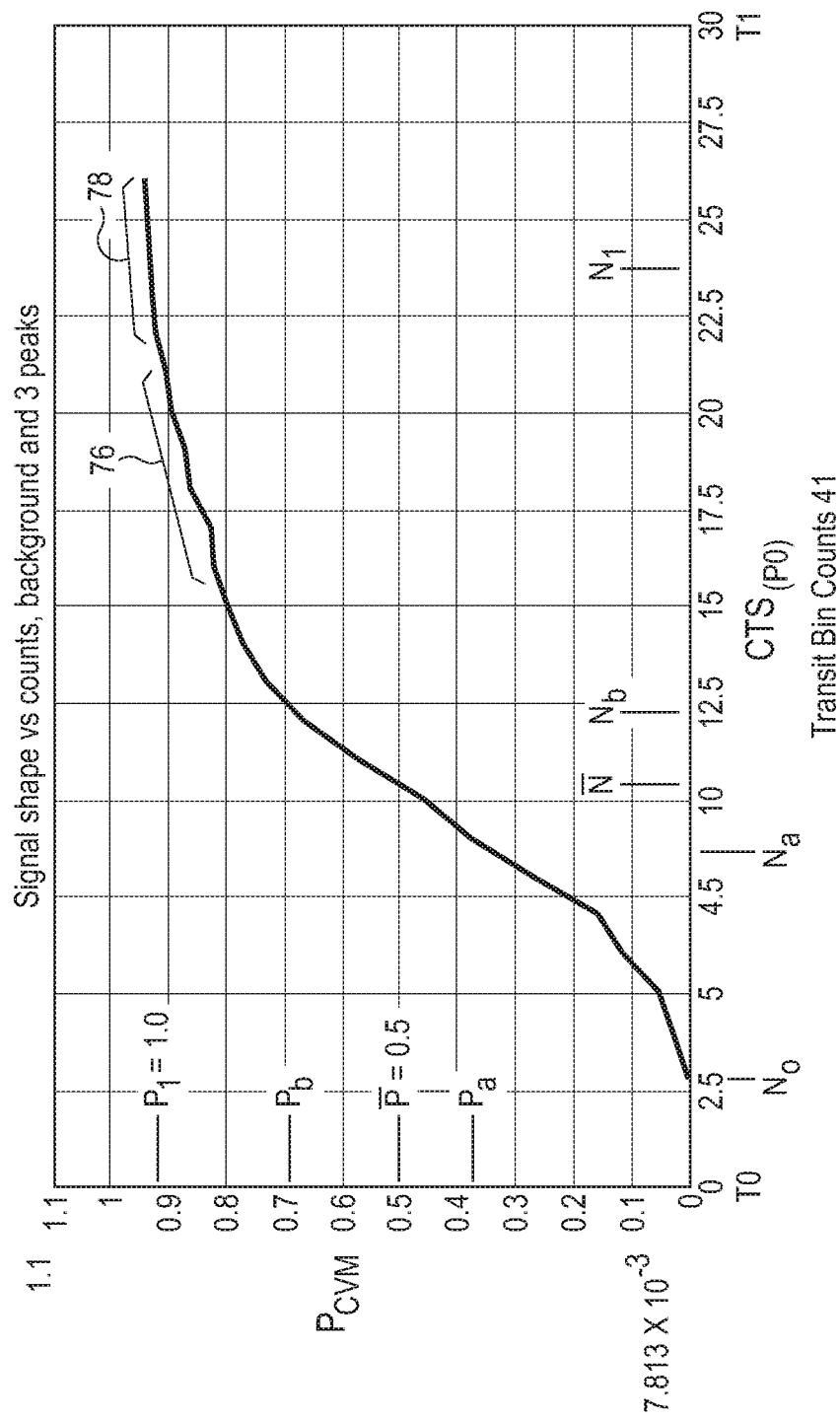
FIG. 7 is a graph of a typical cumulative distribution function for scattering photon counts per 350 μSec period.

Statistical methods are used to accomplish this efficiently. Sampling counts attributable to background noise sources are recorded by the scattering and fluorescence PMTs 42 and 32 contemporaneously with counts attributable to particle transits. While particle transits produce short bursts of photon counts, noise counts are registered at a much lower average rate and are randomly distributed in time. Background counts are reasonably well characterized by Poisson statistics. At higher background noise levels, the distribution of counts around the mean tends towards a Gaussian distribution. If, as depicted in FIG. 7, a cumulative distribution of transit bin data is plotted as a function of transit bin count, a classic S-shaped curve is found that is typical of a Poisson or Gaussian process. With the plateau 76 above the mean corresponding to the transit bin count range above which background noise events are rare. At higher value transit bin counts there is a secondary plateau 78 in the cumulative distribution caused by the passage of highly scattering or fluorescing particles through the excitation beam. This feature occurs further to the right in a plot of cumulative bin statistics, after the noise background has reached its separate cumulative plateau 76. That is, there are two plateaus 76 and 78, in the cumulative distribution as shown in FIG. 7.

Therefore, to determine the average background count rate in real-time, the point on the curve where the cumulative distribution's value is one-half the noise background plateau's value is determined. This is by definition the mean background count rate. The same background protocol is used to calculate background levels in the fluorescence channel. Once the mean values are determined, it is straightforward to estimate the standard deviations of the background counts. This in turn provides a criterion for the scattering channel for detecting particle transits, while avoiding false alarms caused by natural variations in background noise. As a practical matter even if the two plateaus are not well separated, calculation of the mean background and standard deviation are not affected in a material way.

In a preferred embodiment, the particle detection threshold is set at 4 standard deviations above the scattering channel's mean background noise level. The scattering channel transit bin data points corresponding to peak detections identify all particle passages, both biological and non-biological, since all particles scatter light. Net counts for all particle transits are determined by subtracting the fluorescent and scattering channel mean background counts from the measured gross transit bin particle counts for the transit bin data points that correspond to peak detections.

Categorizing and Processing Detections

In a preferred embodiment, particle size is estimated based on electromagnetic scattering theory. The intensity of light scattered by micron-size particles when exposed to collimated UV light scales approximately as the square of particle size. Hence, particle size is approximately proportional to the square-root of the net scattering photons produced when a particle traverses the excitation beam. In an alternative embodiment, actual empirical tests of scattered photon count versus particle size are performed to calibrate the particle size estimation. Armed with particle size information (part of a "particle information set"), particles can be categorized into a set of size bins 50.

The fluorescence counts corresponding in time to each particle scattering event are examined and if these counts are determined to be statistically significant compared to the fluorescence channel background noise, the background counts for the fluorescence channel over the transit period are subtracted from the gross transit counts and this information is also stored for each size category as the net fluorescence for that particle.

In a preferred embodiment, the net fluorescence counts for particles in each size bin are ratiometrically normalized to the corresponding net scattering counts. That is, the net fluorescence counts for the bioaerosol particles are divided by the net scattering counts. In this way, the fluorescence emission intensity is measured relative to the scattering intensity. To a first order, this method eliminates dependence on excitation intensity since both types of photon emission have approximately the same dependence on particle size. For the critical respirable particle size range of 1-10 microns, robust results are achieved by segregating this range into four or more size bins 50. In a preferred embodiment, the bins are defined as ranges of 1 to 2 microns; 2 to 4 microns; 4 to 7 microns; and 7 to 10 microns. However, the number of bins and the size ranges may need to be adjusted to fit different applications.

If this normalization is not done, the fluorescence bins will be too heavily weighted towards counts from large particles. For example, consider the case where the second bin size range above contains two spherical particles, a two-micron diameter particle and a four-micron particle, and where both particles have a fluorescence emission rate per unit area of 1 count per square micron. Then the cumulative fluorescence counts from the two particles in that bin can be calculated to be $20\pi$ counts. A casual observer might then calculate, based on an average particle size of 3 microns, that the fluorescence emission rate per unit area is about 2.22 counts per square micron for the bin, whereas it is only 1 count per square micron, resulting in an estimate that is 2.22 times larger than actual, and a value that mischaracterizes the bin's biological character significantly.

By using the approach described herein, the user has access to the information needed to develop a detailed profile of the surrounding environmental aerosol milieu, including:

Number and size of all aerosol particles

Percentage of aerosol particles that are biological in nature, and their size

Scaled fluorescence intensity of each bioaerosol particle size bin

Background fluorescence and scattering levels

In a preferred embodiment, a rolling average of fluorescent and scattering particle concentrations and fluorescence intensity is maintained over an averaging period of 10 to 60 seconds for each size bin as a baseline or reference for alarm criteria. In a preferred embodiment, if there is a change over the length of one averaging period in the bioaerosol level that is four standard deviations greater than the rolling average, an alarm condition is entered. If the bioaerosol level exceeds a set high value, such as 1000 particles per liter of air, or the fluorescence intensity of a bin exceeds a specified level, then an alarm condition also is entered.

Alternatively, if an aerosol component suddenly appears that has an extremely high ratiometric fluorescence intensity (the ratio of fluorescence signal to scattering signal), this may indicate the presence of a benign manmade agent such as a paper whitening chemical or a natural fluorophore such as a polycyclic aromatic hydrocarbon. The condition may be ignored, or the alarm downgraded to a lower risk level, for example if the ratiometric fluorescence intensity in one or more size bins exceeds a benign fluorescence detection threshold, set at 0.8, or in an alternative embodiment 0.5 of the signal expected from such a reference benign fluorescent aerosol substance. In an alternative embodiment, the threshold for benign fluorescence detection is set relative to the highest ratiometric fluorescence intensity that could be expected from a threatening fluorescent aerosol substance, for example at twice this level. In another preferred embodiment, the benign fluorescence detection threshold is set at a point between the highest expected threatening ratiometric fluorescence intensity and the lowest expected benign ratiometric fluorescence intensity, for example at the midway point between these levels. The ability to monitor not only the bioaerosol concentration but also the intensity of the bioaerosol's fluorescence allows a more nuanced approach to dealing with changes in the suspected bioaerosol background.

In another preferred embodiment, when a sudden large increase in the bioaerosol concentration is detected that causes an alarm, the rolling averages may be frozen at pre-alarm values for a pre-selected time period, such as 2 to 10 minutes so as to prevent this situation from abnormally affecting the rolling average baseline.

The above described method yields great advantage over bioaerosol detectors that use only a count of statistically significant fluorescent signal events to report the presence of a bioaerosol particle and which do not store the actual florescence channel signal strength level during detected particle beam crossings. In the approach described above, the fluorescence intensity may yield information about the type of particle being examined. Also, in systems in which particles are not assigned to size ranges, useful information is lost as to the particle size range containing the largest number of biological aerosol particles.

Noise Processing

In a preferred embodiment, the nominal background signal ("background signal" may also be termed "noise" "background noise" or "background level") levels in each channel and their standard deviations are also tracked. These variables are used in three different ways. First, they provide an ongoing measure of surface contamination and are compared to a caution threshold referenced to a baseline noise level, at the same time as alarm criteria are evaluated, to provide a warning of when the interior surfaces should be cleaned to reduce background noise to a sustainable level. In embodiments, this test evaluates noise levels over an extended period of time, more than an hour, such as a day, week or month as surface contamination tends to build up slowly and is generally a constant and unvarying presence. A baseline noise level may be formed during the first period of operation of device 10, when first put into service or after the most recent cleaning of interior surfaces, and in embodiments, the threshold is formed by multiplying this baseline by a constant (which may also be termed a "background noise increase threshold"). Correction for any other factor that affects noise levels, such as average temperature, is performed in embodiments. Second, background levels may suddenly rise if the sampled air is filled with aerosol particles below the size resolution limit of the system. That is, the sudden presence of a large number of small sampled particles can produce a high background level. A rapid increase in background counts can therefore signal that a high density of small particles has been encountered, and this information may be transmitted to the user. This allows the presence of particles that are smaller than the system size resolution limit to be detected in a qualitative or ratiometric manner. Independent of any specific size resolution limit, if the inferred fluorescent or scattering channel background noise increases by a factor of 2 times or more over one averaging period, or by a statistically unlikely amount, such as, in embodiments, either three or four standard deviations, it is presumed that this is due to a significant increase in small particle concentration, and personnel are notified by a display or a sound. In alternative preferred embodiments, the test for notifying personnel is calibrated by the absolute level of the initial background noise and environmental conditions, which are either sensed by other systems and communicated to device 10, or entered by personnel.

Detecting Photon Flood at the Scattering Channel PMT

Referring to FIG. 3, At the output of scatter channel PMT 42, each photon encounter appears as a pulse, which is then registered by counter 38. But if a second photon encounter begins before the pulse from a first photon encounter has transitioned back to zero, then the two pulses appear as one, and only one photon encounter is detected and counted by counter 38. If a constant stream of photons is being encountered by scattering PMT 42, this results in a DC signal at its output, and counter 38 will only register a detection when there is a gap in the photon stream. To avoid being misled by this condition, a DC detector 88 is placed in parallel with counter 38. When a continuous DC high-state signal is detected, a fault alarm warning is relayed to the user.

Ease of Cleaning

Figure 8:
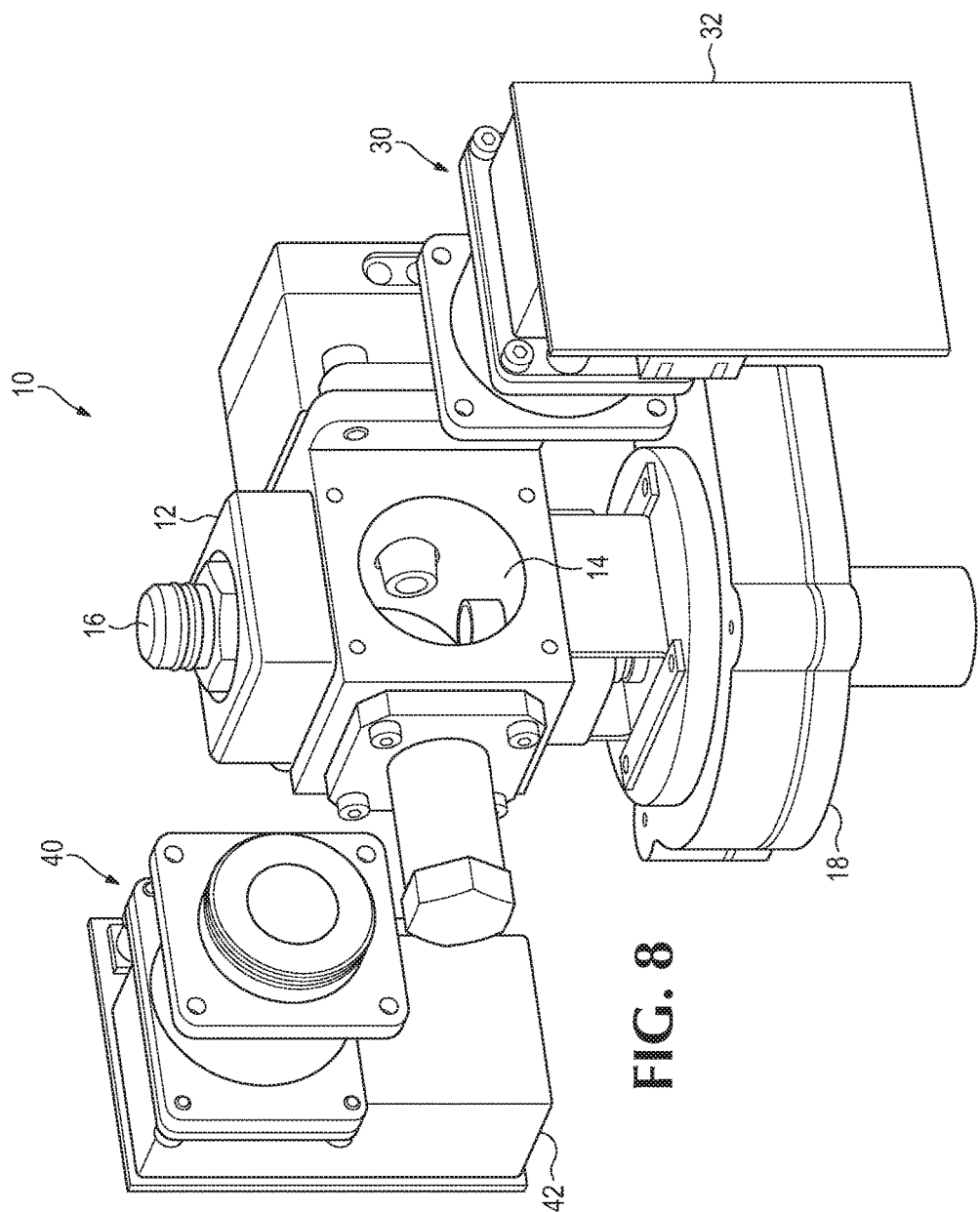
FIG. 8 is a view of the detector of FIG. 1, partially disassembled for cleaning.

Referring to FIG. 8, in the detector 10 described here, each optics channel 30 and 40 can be mounted as a separate sealed assembly that can be removed as a single unit from the central module that contains the particle and light beam forming components (FIGS. 1-3). Although not shown, in one embodiment each channel is bolted onto the rest of the housing using the bolt-holes shown. The planar faces of lenses 82 and 92 are the most likely surfaces to be affected by fouling, and by organizing the optical system's physical structure in this way, each of the two critical light-capturing lens faces may be easily cleaned with minimal risk of scratches and residual surface debris, similar to cleaning the front lens face on a camera. This is a very critical issue for applications where the devices may be exposed to dusty inorganic aerosols such as clay and sand. Even if precautions are taken to minimize dust accumulation on the light capturing optical faces there will typically be some aerosols that reach these surfaces, such as during startup and shutdown of the sampling airflow when the airflows may become temporarily turbulent.

While a number of exemplary aspects and embodiments have been discussed above, those possessed of skill in the art will recognize certain modifications, permutations, additions and sub-combinations thereof. It is therefore intended that the following appended claims, and claims hereafter introduced, are interpreted to include all such modifications, permutations, additions and sub-combinations as are within their true spirit and scope.

The invention claimed is:

1. A bioaerosol detector, comprising:
   (a) a housing defining a chamber;
   (b) an air stream injection assembly, producing an airstream with entrained particles having an average velocity within a transverse extent, in said chamber;
   (c) a light source, producing a light beam that intersects and crosses said air stream;
   (d) a light detection assembly, configured and positioned to detect light generated by scattering of light from said light beam, by particles in said air stream;
   (e) a digitizer, which produces a sequence of first digital values, representative of light detection, responsive to said light detection assembly;
   (f) a data processor that repeatedly calculates a background noise level, responsive to said sequence of first digital values, and which is responsive to a high density of small particles condition wherein said noise level rises due to small particles in said air stream that are not detected and are sufficiently numerous to raise the noise level, thereby obscuring said particles from detection, by detecting a condition in which said noise level has risen above a threshold.

2. The bioaerosol detector of claim 1, wherein:
   (a) said light source is an ultraviolet light source;
   (b) said light detection assembly is a scattered light detection assembly, including a short pass filter, and which detects shorter wavelength light; and
   (c) further comprising a fluorescence light detection assembly, including a long wavelength filter, and which detects longer wavelength light indicative of light that has been created by biofluorescence, from said particles in said air stream.

3. The bioaerosol detector of claim 2, wherein a comparison of fluorescent returns and scattering returns is performed for a time period in which a high density of undetected small particles condition is detected.

4. The bioaerosol detector of claim 1, wherein said detector further includes a human perceptible notification device and wherein said device issues a human perceptible notification when a high density of small particles condition is detected.

5. The bioaerosol detector of claim 1, wherein said background noise level is responsive to said sequence of first digital values by being based on a sequence of summed digital values, each summed digital value being a summation of a set of first digital values.

6. A bioaerosol detector, comprising:
(a) a housing defining a chamber;
(b) an air stream injection assembly, producing an airstream with entrained particles having an average velocity within a transverse extent, in said chamber;
(c) a light source, producing a light beam that intersects with and crosses said air stream;
(d) a photon detection assembly, including an optical train and a photon detector, and being configured and positioned to generate an output pulse in response to a photon encounter, from light emitted from said light source and scattered by a particle in said air stream;
(e) a digitizer, responsive to said photon detector, to produce a sequence of first digital values, each first digital value representing detections of output pulses from said photon detection assembly, per a unit of time duration;
(f) a photon detector continuous high state sensor, also responsive to said photon detection assembly, and adapted to detect a continuous high output state, thereby indicating that a flood of photons is preventing said photon detector from transitioning into a low state between photon encounters.

7. The bioaerosol detector of claim 6, wherein said digitizer detects output pulses by detecting rising edges.

8. The bioaerosol detector of claim 6, wherein said digitizer detects output pulses by detecting falling edges.

9. The bioaerosol detector of claim 6, wherein:
(a) said light source is an ultraviolet light source;
(b) said light detection assembly is a scattered light detection assembly, including a short pass filter, and which detects shorter wavelength light; and
(c) further comprising a fluorescence light detection assembly, including a long wavelength filter, and which detects longer wavelength light indicative of light that has been created by biofluorescence from said particles in said air stream.

10. A particle detector, comprising:
(a) a housing defining a chamber;
(b) an air stream injection assembly, producing an airstream, having a transverse extent, in said chamber;
(c) a light source, producing a light beam that intersects with and crosses said air stream;
(d) a light detection assembly, configured and positioned to detect scattering of light from said light beam, by particles in said air stream;
(e) a digitizer, responsive to said light detection assembly, to produce a sequence of first digital values, each first digital value representing light detected per a unit of time duration;
(f) a data processing assembly, computing a background noise estimation, responsive to said sequence of digital values, and repeatedly determining if interior surfaces of said light detection assembly have become degraded by adherent particles by analyzing changes to said background noise estimation over time to determine if an increase in background noise above a background noise increase threshold has taken place over a time period longer than a time period threshold.

11. The particle detector of claim 10, wherein
(a) said light source is an ultraviolet light source and
(b) wherein said light detection assembly is a scattered light detection assembly, including a short pass filter, and which detects shorter wavelength light; and
(c) further comprising a fluorescence light detection assembly, including a long wavelength filter, and which detects longer wavelength light indicative of light that has been created by biofluorescence from said particles in said air stream.

12. The particle detector of claim 10, wherein the background noise level is assessed for a period of greater than an hour, to determine if there has been a degradation of interior surfaces above a threshold amount.

13. The particle detector of claim 10, wherein said background noise level is responsive to said sequence of first digital values by being based on a sequence of summed digital values, each summed digital value being a summation of a set of first digital values.

14. A method of detecting bioaerosols, comprising:
(a) detecting particles and estimating a particle size for each detected particle;
(b) determining a fluorescence strength for each detected particle;
(c) comparing particle size and fluorescence strength for each detected particle to arrive at a normalized fluorescence strength per particle;
(d) comparing normalized fluorescence strengths over a time period to a maximum threshold, to detect highly fluorescent manmade substances.

15. The method of claim 14, wherein a human perceptible notification device issues an advisory, upon the detection of a highly fluorescent manmade substance.

16. The method of claim 14, wherein said threshold is set in reference to the highest level of fluorescence return, relative to particle size, expected from a threatening fluorescent particle.

17. The method of claim 14, wherein said particle detection is performed by illuminating particles in an air stream, passing through a chamber, with ultraviolet light, and detecting and digitizing a resultant light signal, and wherein said fluorescence strength determination is performed by long pass filtering, detecting and digitizing a resultant light signal, and wherein said steps of comparing are performed digitally in a digital computer.

18. A bioaerosol detector, comprising:
(a) a housing defining a chamber;
(b) an air stream injection assembly, producing an airstream with entrained particles having an average velocity within a transverse extent, in said chamber;
(c) an ultraviolet light source, producing a light beam that intersects said air stream;
(d) a scattering light detection assembly, configured and positioned to detect light generated by scattering of light from said light beam, by particles in said air stream, and including a first lens that has a surface facing said chamber;
(e) a fluorescence light detection assembly, including a long wavelength filter, and which detects longer wavelength light indicative of light that has been created by biofluorescence, from said particles in said air stream, and including a second lens that has a surface facing said chamber; and
(f) wherein said scattering light detection assembly can be removed as a single unit, thereby permitting easy access to said first lens, to permit cleaning of said lens.

19. The bioaerosol detector of claim 18, wherein said fluorescence light detection assembly can be removed as a single unit, thereby permitting easy access to said second lens, to permit cleaning of said lens.

20. The bioaerosol detector of claim 18, wherein said scattering light detection assembly is bolted on to said housing, and may be removed by undoing bolts.

* * * * *